(12) United States Patent
Waldorf et al.

(10) Patent No.: US 9,101,312 B2
(45) Date of Patent: *Aug. 11, 2015

(54) SYSTEM FOR THE PHYSIOLOGICAL EVALUATION OF BRAIN FUNCTION

(71) Applicant: TBI Diagnostics LLC, Scottsdale, AZ (US)

(72) Inventors: Ronald A. Waldorf, Beverly Hills, CA (US); Hirsch Handmaker, Scottsdale, AZ (US)

(73) Assignee: TBI DIAGNOSTICS LLC, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/184,465

(22) Filed: Feb. 19, 2014

(65) Prior Publication Data

US 2014/0171756 A1  Jun. 19, 2014

Related U.S. Application Data

(63) Continuation-in-part of application No. 13/450,230, filed on Apr. 18, 2012, now Pat. No. 8,668,337.

(51) Int. Cl.
| | |
|---|---|
| *A61B 3/14* | (2006.01) |
| *A61B 3/10* | (2006.01) |
| *A61B 3/00* | (2006.01) |
| *A61B 5/16* | (2006.01) |
| *A61B 5/00* | (2006.01) |

(Continued)

(52) U.S. Cl.
CPC ................. *A61B 5/16* (2013.01); *A61B 3/0083* (2013.01); *A61B 3/032* (2013.01); *A61B 3/113* (2013.01); *A61B 5/4005* (2013.01)

(58) Field of Classification Search
CPC .... A61B 3/113; A61B 3/0025; A61B 3/0091; A61B 3/112
USPC .................................................. 351/200–246
See application file for complete search history.

(56) References Cited

U.S. PATENT DOCUMENTS

| | | | |
|---|---|---|---|
| 4,850,691 | A | 7/1989 | Gardner et al. |
| 5,422,689 | A | 6/1995 | Knapp et al. |

(Continued)

OTHER PUBLICATIONS

In the US Patent and Trademark Office U.S. Appl. No. 13/450,230 Non-Final Office Action dated Aug. 27, 2013, 5 pages.

(Continued)

*Primary Examiner* — Mohammed Hasan
(74) *Attorney, Agent, or Firm* — Squire Patton Boggs (US) LLP

(57) ABSTRACT

The OculoKinetic Device is used to test an individual to evaluate brain function including, but not limited to, identifying the presence of a traumatic brain injury or central nervous system disease which manifests itself through abnormal ocular responses to stimuli by using the high-speed tracking of an individual's eye movements (monocular or binocular, and either conjugate or disconjugate in horizontal, vertical, or torsional directions or combinations thereof), pupil size and reactivity, eyelid position, and blink parameters, and optionally along with other ocular elements, i.e., eyeball pressure, temperature, blood flow, etc. The eye movement stimulus protocol uses a target that moves in any direction of a two- or three-dimensional plane and may use a color display or geometric shapes. In addition, the stimuli can be used in conjunction with cognitive testing, balance assessment, and other non-eye tests.

29 Claims, 8 Drawing Sheets

(51) Int. Cl.
*A61B 3/032* (2006.01)
*A61B 3/113* (2006.01)

(56) References Cited

U.S. PATENT DOCUMENTS

| | | | |
|---|---|---|---|
| 5,490,098 A | | 2/1996 | Kardon |
| 5,517,021 A | | 5/1996 | Kaufman et al. |
| 5,649,061 A | * | 7/1997 | Smyth .................... 706/16 |
| 5,661,538 A | | 8/1997 | Carter |
| 6,022,109 A | | 2/2000 | Dal Santo |
| 6,260,968 B1 | | 7/2001 | Stark et al. |
| 6,669,651 B1 | | 12/2003 | Fukushima et al. |
| 6,820,979 B1 | | 11/2004 | Stark et al. |
| 7,083,280 B2 | | 8/2006 | Hakamata |
| 7,147,327 B2 | | 12/2006 | Stark et al. |
| 7,384,399 B2 | | 6/2008 | Ghajar |
| 7,614,743 B2 | | 11/2009 | Geiger |
| 7,614,745 B2 | | 11/2009 | Waldorf et al. |
| 7,651,224 B2 | | 1/2010 | Wood et al. |
| 7,665,845 B2 | | 2/2010 | Kiderman et al. |
| 7,670,002 B2 | | 3/2010 | Stark et al. |
| 7,708,700 B2 | | 5/2010 | Ghajar |
| 7,731,360 B2 | | 6/2010 | MacDougall et al. |
| 7,753,523 B2 | | 7/2010 | Kiderman et al. |
| 7,753,526 B2 | | 7/2010 | Todd |
| 7,819,818 B2 | | 10/2010 | Ghajar |
| 7,854,511 B2 | | 12/2010 | Molnar et al. |
| 7,866,818 B2 | | 1/2011 | Schroeder et al. |
| 7,967,442 B2 | | 6/2011 | Siminou |
| 7,988,287 B1 | * | 8/2011 | Butler et al. .................... 351/210 |
| 8,048,002 B2 | | 11/2011 | Ghajar |
| 8,109,633 B2 | | 2/2012 | Molnar et al. |
| 8,235,526 B2 | | 8/2012 | Stark et al. |
| 8,500,277 B1 | | 8/2013 | Butler et al. |
| 8,534,840 B2 | | 9/2013 | Siminou |
| 8,585,589 B1 | | 11/2013 | Cinberg |
| 8,585,609 B2 | | 11/2013 | Kiderman et al. |
| 8,668,337 B2 | * | 3/2014 | Waldorf et al. ............... 351/209 |
| 2008/0013047 A1 | | 1/2008 | Todd et al. |
| 2008/0024724 A1 | | 1/2008 | Todd |
| 2008/0043201 A1 | | 2/2008 | Todd |
| 2008/0049187 A1 | | 2/2008 | Joos et al. |
| 2008/0192202 A1 | | 8/2008 | Lewkowski |
| 2009/0216092 A1 | | 8/2009 | Waldorf et al. |
| 2010/0092049 A1 | | 4/2010 | Schroeder et al. |
| 2010/0094161 A1 | | 4/2010 | Kiderman et al. |
| 2011/0058144 A1 | | 3/2011 | Molnar et al. |
| 2011/0176106 A1 | | 7/2011 | Lewkowski |
| 2012/0330178 A1 | | 12/2012 | Kraft et al. |
| 2013/0278899 A1 | | 10/2013 | Waldorf et al. |

OTHER PUBLICATIONS

Donaghy et al.; "Eye movements in amyotrophic lateral sclerosis and its mimics: a review with illustrative cases," *J Neurol Neurosurg Psychiatry*, 2011; 82(1):110-116, January.

Ghajar, Jamshid; Eye-Tracking Rapid Attention Computation (Eye-TRAC), http://www.clinicaltrials.gov/ct2/show/NCT00743821, Dec. 2012.

Irving et al.; "Horizontal Saccade Dynamics across the Human Life Span," *Investigative Ophthalmology & Visual Science*, 2006; 47(6); 2478-2484, September.

Maruta et al.; "Visual tracking synchronization as a metric for concussion screening," *J Head Trauma Rehabil*, 2010; 25(4):293-305, September.

Ross et al.; "Saccadic eye movements in normal children from 8 to 15 years of age: A developmental study of visuospatial attention," *Journal of Autism and Developmental Disorders*, 1994; 24(4):413-431, June.

Zackon et al.; "Smooth pursuit in senescence: Effects of Target Acceleration and Velocity," *Acta Otolaryngol*, 1987; 104(3-4); 290-297, June.

\* cited by examiner

SYSTEM FOR THE PHYSIOLOGICAL EVALUATION OF BRAIN FUNCTION

CROSS-REFERENCE TO RELATED APPLICATIONS

This application is a continuation-in-part of U.S. patent application Ser. No. 13/450,230, titled "System for the Physiological Evaluation of Brain Function" filed on Apr. 18, 2012, now U.S. Pat. No. 8,668,337 B2 issued Mar. 11, 2014.

FIELD OF THE INVENTION

This invention relates to a system that is used to test an individual to evaluate brain functions including, but not limited to, identifying the presence of a traumatic brain injury or other central nervous system diseases which manifest themselves through abnormal ocular responses to stimuli, where the system uses high-speed tracking of an individual's eye movements, pupil size and reactivity, eyelid position and blink parameters, iris characteristics, and optionally other ocular elements, i.e., eyeball pressure, temperature, blood flow, etc.

BACKGROUND OF THE INVENTION

It is a problem in the field of the neurophysiology of brain injuries to provide a method and apparatus that can be used to quickly, accurately, and non-invasively evaluate an individual to identify the presence of Traumatic Brain Injury (TBI) and its variants, also known as Minimal Traumatic Brain Injury (mTBI), more commonly known as concussion (collectively termed "TBI" herein).

TBI is the leading cause of death and disability for America's youth. According to statistics from the Centers for Disease Control and Prevention (CDC), between one million and four million new brain injuries occur every year in America due to trauma in sports and recreational activities. More than 767,000 American youth visit the emergency room because of traumatic brain injuries each year. Of those, more than 80,000 are hospitalized and more than 11,000 die. This at-risk population is only now gaining recognition and awareness, as most youth sports activities take place with no health care professionals in attendance, and few programs are available to determine which players suffer a concussion or when they should return to play after this injury. While professional sports, such as the National Football League (NFL), Major League Baseball (MLB), and National Hockey League (NHL), are implementing safety and monitoring standards, even they are utilizing only one or two of the quartet of commercially available tests which are known to be of value for adequate assessment and management of patients with TBI: physical examination by a qualified healthcare professional; neurocognitive testing; balance assessment; and ocular responses. The frequency and sequelae of concussions have garnered national and international media attention, and has reached epidemic proportions, with these events now documented to be of greatest significance in younger (6- to 14-year-old) athletes whose brains have not yet become fully developed ("myelinated"). Note that sequelae of TBI include headache and dizziness, anxiety, apathy, depression, aggression, cognitive impairments, personality changes, mania, and psychosis. Typically, a sequela is a chronic condition that is a complication of an acute condition that begins during the acute condition.

Prior scientific research shows that eye movements are affected by these types of traumatic events. Although the research presents findings which support this hypothesis, the presently available equipment, test protocols, and analysis protocols are limited in several important respects and fail to provide an effective tool for detecting and monitoring TBI, especially in a competitive sports field or combat setting.

BRIEF SUMMARY OF THE INVENTION

The present System For The Physiological Evaluation Of Brain Function (termed "OculoKinetic Device" herein) provides a method and apparatus that is used to quickly, accurately, and non-invasively identify and evaluate a test subject to identify the status of brain function including the presence of Traumatic Brain Injury (TBI) and its variants, also known as Minimal Traumatic Brain Injury (mTBI), or a disease which manifests itself through abnormal ocular responses to stimuli.

The OculoKinetic Device uses the high-speed tracking of a set of physiological parameters of a test subject, which can include: eye movements (monocular or binocular, and either conjugate or disconjugate in horizontal, vertical, or torsional directions, or combinations thereof); pupil size, shape, and reactivity; eyelid position and blink parameters; and optionally along with other ocular elements, i.e., eyeball pressure, temperature, blood flow, etc. The measurements can include determining how the test subject responds to visual stimuli which can move on a stimulus presentation display in at least one of: a random pattern, discontinuous movement, and an oblique direction or where the visual stimuli are geometric shapes, multi-colored images, or flashing images. Prior stored test results for the test subject are used to provide an individualized baseline for the test subject thereby to evaluate the difference between the test subject's present condition and a prior state or the difference between the test subject's present test measurements and multiple prior test measurements to determine a trend for the test subject over time. In addition, the test subject can be unambiguously identified by means of an iris scan biometric, as is known in the art, to ensure the accuracy of the evaluation by authenticating the identity of the test subject.

BRIEF DESCRIPTION OF THE DRAWINGS

FIG. 2 illustrates a cross-section view of typical components used to implement the test subject interface;

DETAILED DESCRIPTION OF THE INVENTION

Figure 1:
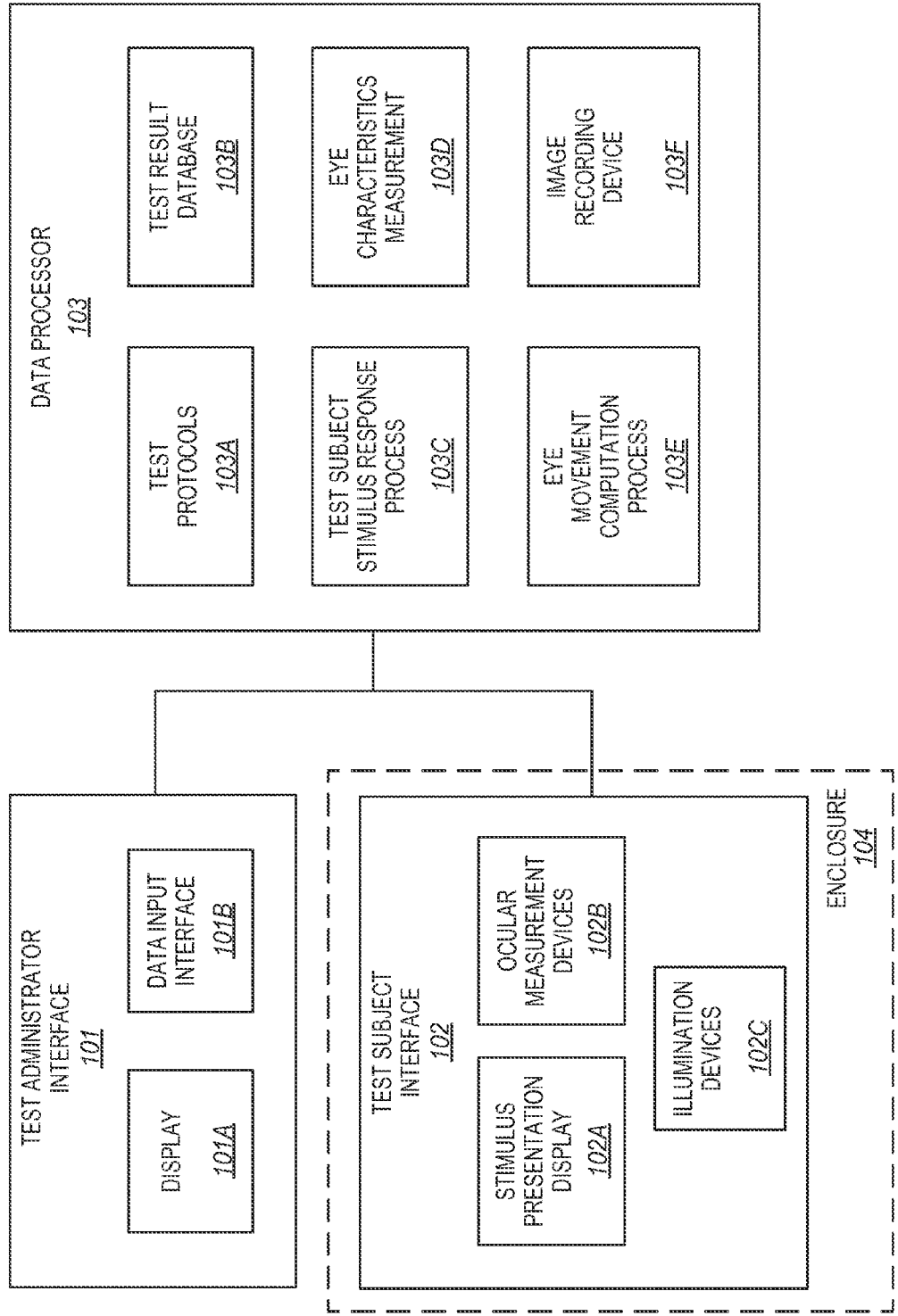
FIG. 1 illustrates, in block diagram form, the overall architecture of the present OculoKinetic Device.

The prior art is replete with publications that relate to eye movements, techniques for eye tracking, pupillography, and iris identification as a biometric measurement. However, these publications each provide an isolated perspective of a particular aspect of the technology; and the prior art is devoid of the provision of an enhanced, inclusive system that can quickly, accurately, and non-invasively identify and evaluate a test subject to identify the status of their brain function, including the presence of Traumatic Brain Injury (TBI) and its variants.

The ideal system for the physiologic evaluation of brain function has the following features: self-diagnostics to ensure each test is being performed within pre-defined specification limits; ability to accurately identify the test subject, stimulus paradigms, and test results in a manner that meets the requirements for human subject medical applications; and it must meet the criterion for functional testing in ambient environments that are variable in terms of brightness/sunlight, weather, temperature, noise, and other testing constraints.

The present OculoKinetic Device measures a set of test subject physiological parameters, which can include: an individual's eye movements (monocular or binocular, and either conjugate or disconjugate in horizontal, vertical or torsional directions, or combinations thereof); pupil size, shape, and reactivity; and eyelid position and blink parameters, which optionally can be combined with other ocular elements, i.e., eyeball pressure, temperature, blood flow, etc. In order to determine the presence of abnormal ocular responses to visual stimuli, the OculoKinetic Device produces an eye movement stimulus protocol that moves a visual target in any direction of a two- or three-dimensional plane on a stimulus presentation device. For example, with a Smooth Pursuit test, instead of a target moving in a horizontally only or a vertically only direction, it may move the visual target in a FIG. 8 pattern or a more complex, randomized pattern on the stimulus presentation device. The target representation is not limited to just black and white images. It may turn out that certain brain injuries and/or illnesses are more accurately detected by using colored dots, stripes, etc. In addition, the use of symbols in the visual target is anticipated, where the visual stimuli are geometric shapes, multi-colored images, flashing images, etc. Such diversity is beneficial in the testing of children who are more capable of describing shapes and colors than black and white dots or lines.

In addition, visual stimuli can be used in conjunction with cognitive testing. As one of many possibilities, the Saccade test could be done with dots of a certain color, i.e., blue. The test subject is instructed to look only at blue dots. Some of the dots would be presented in blue, but others could be red, yellow, etc. By seeing how the test subject's eye(s) move(s) or fail(s) to move, and analyzing the "errors," a more accurate test of possible brain trauma may be established.

This concept works for all of the above-noted test stimuli, i.e., instead of gazing just to the left, or right, or up, or down, the proposed stimuli would have a subject gaze to the upper right, lower left, etc. Saccade testing could have saccades (or point-to-point eye movements) that are truly two-dimensional. Another embodiment could have a visual target moving "toward" or "away" from the test subject in order to evaluate ocular responses of vergence or accommodation, as one example.

Ocular Physiology

The extraocular muscles are the three pairs of muscles that control the movements of the human eye. The actions of the extraocular muscles depend on the position of the eye at the time of muscle contraction.

| Muscle | Innervation | Origin | Insertion | Primary function | Secondary function | Tertiary function |
|---|---|---|---|---|---|---|
| Superior rectus | Superior branch of oculomotor nerve | Annulus of Zinn from tendinous ring | eye (anterior, superior surface) | Elevation | Intorsion | Adduction |
| Inferior rectus | Inferior branch of oculomotor nerve | Annulus of Zinn from tendinous ring | eye (anterior, inferior surface) | Depression | Extorsion | Adduction |
| Lateral rectus | Abducens nerve | Annulus of Zinn from tendinous ring | eye (anterior, lateral surface) | Abduction | | |
| Medial rectus | Inferior branch of oculomotor nerve | Annulus of Zinn from tendinous ring | eye (anterior, medial surface) | Adduction | | |
| Superior oblique | Trochlear nerve | Superior and Medial to Annulus of Zinn via the Trochlea of superior oblique which forms a "pulley system" | eye (posterior, superior, lateral surface) | Intorsion | Depression | Abduction |
| Inferior oblique | Inferior branch of oculomotor nerve | Maxillary bone | eye (posterior, inferior, lateral surface) | Extorsion | Elevation | Abduction |

Eye Movements

The physiological reason for this is that it has been known for many decades that there are three pairs of brain nuclei and associated neurological tracks that control the three pairs of muscles that innervate the eye; and these tracks are bilateral, i.e., represented in a coordinated manner for each eye. As a simple example, when the right eye moves right, the lateral muscle pulls the right eye toward the right, and the medial muscle of the right eye loosens its contraction of the eye to allow the eye to move right. At the same time, the opposite situation is occurring with the left eye, i.e., it is the medial muscle that contracts to move the left eye to the right and the lateral muscle of the left eye loosens its contraction of the eye to allow the eye to move right. This same scenario exists for vertical eye movements and for the most complicated eye movements, which are the oblique and torsional eye movements.

Figure 8:
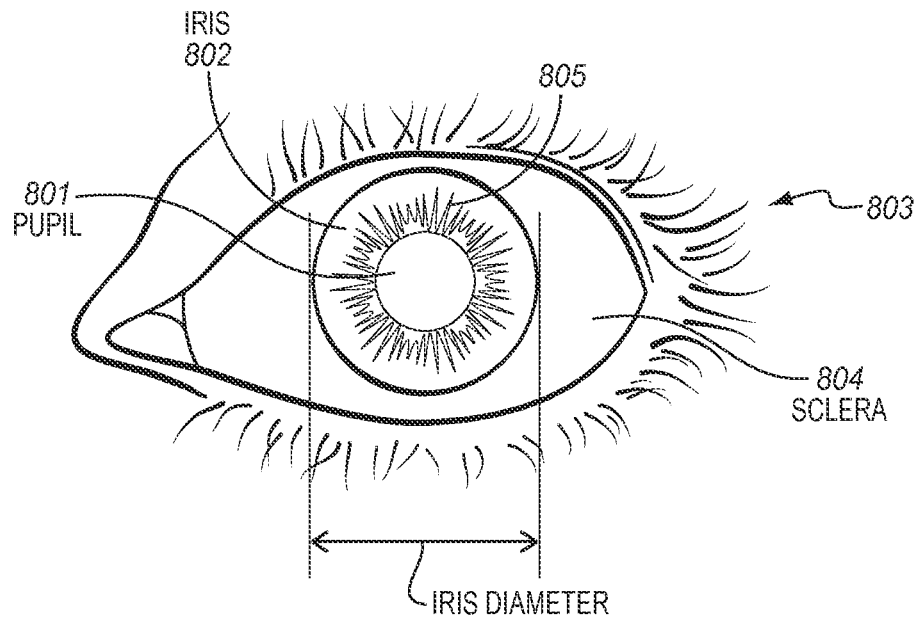
FIG. 8 is a drawing illustrative of typical pupil calibration measurements used in the OculoKinetic Device.

As shown in FIG. 8, the sclera 804, also known as the white of the eye, is the opaque, fibrous, protective, outer layer of the eye 803 containing collagen and elastic fiber. In humans, the entire sclera 804 is white, contrasting with the colored iris 802. The sclera 804 forms the posterior five-sixths of the connective tissue coat of the globe. It is continuous with the dura mater and the cornea, and maintains the shape of the globe, offering resistance to internal and external forces, and provides an attachment for the extra-ocular muscle insertions.

The iris 802 is a thin, circular structure in the eye, responsible for controlling the diameter and size of the pupil 801 and thus the amount of light reaching the retina. The color of the iris 802 often is referred to as "eye color." In optical terms, the pupil 801 is the eye's aperture, and the iris 802 is the aperture stop. The iris 802 consists of two layers: the front pigmented fibrovascular tissue known as a "stroma" and, beneath the stroma, pigmented epithelial cells. The stroma connects to a sphincter muscle (sphincter pupillae), which contracts the pupil 801 in a circular motion, and a set of dilator muscles (dilator pupillae) which pull the iris 802 radially to enlarge the pupil 801, pulling it in folds. The back surface is covered by a heavily pigmented epithelial layer that is two cells thick (the iris pigment epithelium), but the front surface has no epithelium. This anterior surface projects as the dilator muscles. The high pigment content blocks light from passing through the iris 802 to the retina, restricting it to the pupil 801. The outer edge of the iris 802, known as the "root," is attached to the sclera and the anterior ciliary body. The iris 802 and ciliary body together are known as the "anterior uvea."

The retina (not shown) is a light-sensitive layer of tissue lining the inner surface of the eye 803. The optics of the eye create an image of the visual world on the retina (through the cornea and lens), which serves much the same function as the film in a camera. Light striking the retina initiates a cascade of chemical and electrical events that ultimately trigger nerve impulses. These are sent to various visual centers of the brain through the fibers of the optic nerve.

Cognition

There are many different ways of assessing cognition, i.e., present cognition vs. anticipatory cognition. Since, by its own nature, cognition really is not an involuntary, hard-wired, brain response, but integrates several neurological elements to achieve the response, this disclosure focuses on those cognitive functions that are closely related to the involuntary oculomotor and/or pupillary responses of the eye. One possible unique opportunity is to have the eye movement become the cognitive function, i.e., move the red dot into the yellow square by focusing on the dot and making the appropriate eye movement to move it toward and then into the yellow square. The time frame for completion of the task, the accuracy of the "line of sight" movement to the box, and the eventual endpoint of dot placement within the box may be as significant, if not more so, than the current cognitive tests which are mainly based on hearing instructions, visual processing of the information, and a manual interaction with the computer, paper, etc., to give an answer. In addition, pupillary responses can be tracked by automatically tracking the size, location, and responsiveness of a subject's pupil(s) in response to a set of stimuli as shown in US Patent Application Publication No. US2009/0216092 A1. By just using the eyes and brain processing, the OculoKinetic Device provides a novel/better/quicker way to assess the current function of the central nervous system in the test subject resulting from head injuries.

The following description uses TBI as the example to illustrate the operation of the present OculoKinetic Device, but it is not limited to these applications, since it should be noted that the following diseases have also been reported to manifest themselves via ocular abnormalities which are detectable on ocular examinations:

1. Alzheimer's Disease;
2. Multiple Sclerosis;
3. Parkinson's Disease; and
4. Amyotrophic Lateral Sclerosis (ALS)—"Lou Gehrig Disease."

OculoKinetic Device Operational Architecture

To monitor the movements of the test subject's eyes, ocular measurement devices, some of which may be sensitive in the near infrared illumination spectrum, or use Wave Front technology, etc., are positioned in the field of vision of the test subject to record the test subject's eye movements during testing. These ocular measurement devices are housed in a test subject interface which can be in the form of any of several goggle or head-mounted configurations or positioned in a "Viewport." In addition, a stimulus presentation device is included in the test subject interface to display visual stimuli for the test subject. To maximize the efficacy of these measurements, it is imperative that the configuration of the ocular measurement devices, the stimulus presentation device, and the test subject be arranged in a manner that controls the ambient light impinging on the test subject's eyes, as well as the elimination of extraneous visual targets from the test subject's field of vision, as is illustrated in the prior art. All of this must be accomplished in an ergonomic manner such that the test subject can be tested easily in a quick and efficient manner, regardless of the environment around them, i.e., stadium field of play, combat zone, etc.).

FIG. 1 illustrates, in block diagram form, the overall architecture of the present OculoKinetic Device 100, which includes a Test Administrator Interface 101, a Test Subject Interface 102, and a Data Processor 103. Another embodiment would be an OculoKinetic Device 100 that is fully automated—not requiring an operator. The division of functionality illustrated herein is simply for the purpose of teaching the claimed invention and is not a limitation on the implementation of a system that embodies the novel functionality of the OculoKinetic Device 100. As an example, the Test Administrator Interface 101 includes a Data Input Interface 101B for use by the test administrator and a Display 101A for presenting test result information to the test administrator. The Test Subject Interface 102 includes an Enclosure 104 which encloses both a Stimulus Presentation Display 102A, which displays a set of visual stimuli for the test subject, and Ocular Measurement Devices 102B, which measure a set of test subject physiological parameters and the test subject's ocular responses to the visual stimuli. In addition, a Data Processor 103 is connected to both the Test Administrator Interface 101 and the Test Subject Interface 102. The Data Processor 102 includes a number of processes and databases (which can be implemented external to the Data Processor 103) for executing the tests and processing the resultant test subject measurement data. The Data Processor 103 includes Test Protocols 103A, Test Result Database 103B, Test Subject Stimulus Response Process 103C, Eye Characteristics Measurement 103D, Eye Movement Computation Process 103E, and Image Recording Device 103F as are described in additional detail below.

Enclosure

Rather than trying to control the ambient light of the room/test site or appearance of surrounding visible items that may confound the test subject's concentration on the visual targets presented on the Stimulus Presentation Display 102A and/or the size of the Test Subject's pupil, an enclosure 104 (not shown in detail) is configured to enclose the Stimulus Presentation Display 102A and Ocular Measurement Devices 102B, as well as to securely position the test subject's head and contact areas around the subject's facial area. The headset shown in FIG. 2 has a faceplate 141 against which the test subject 105 places their face and which may or may not include a chin rest to further support the head of the test subject.

Stimulus Presentation and Ocular Response Measurement

Figure 2:
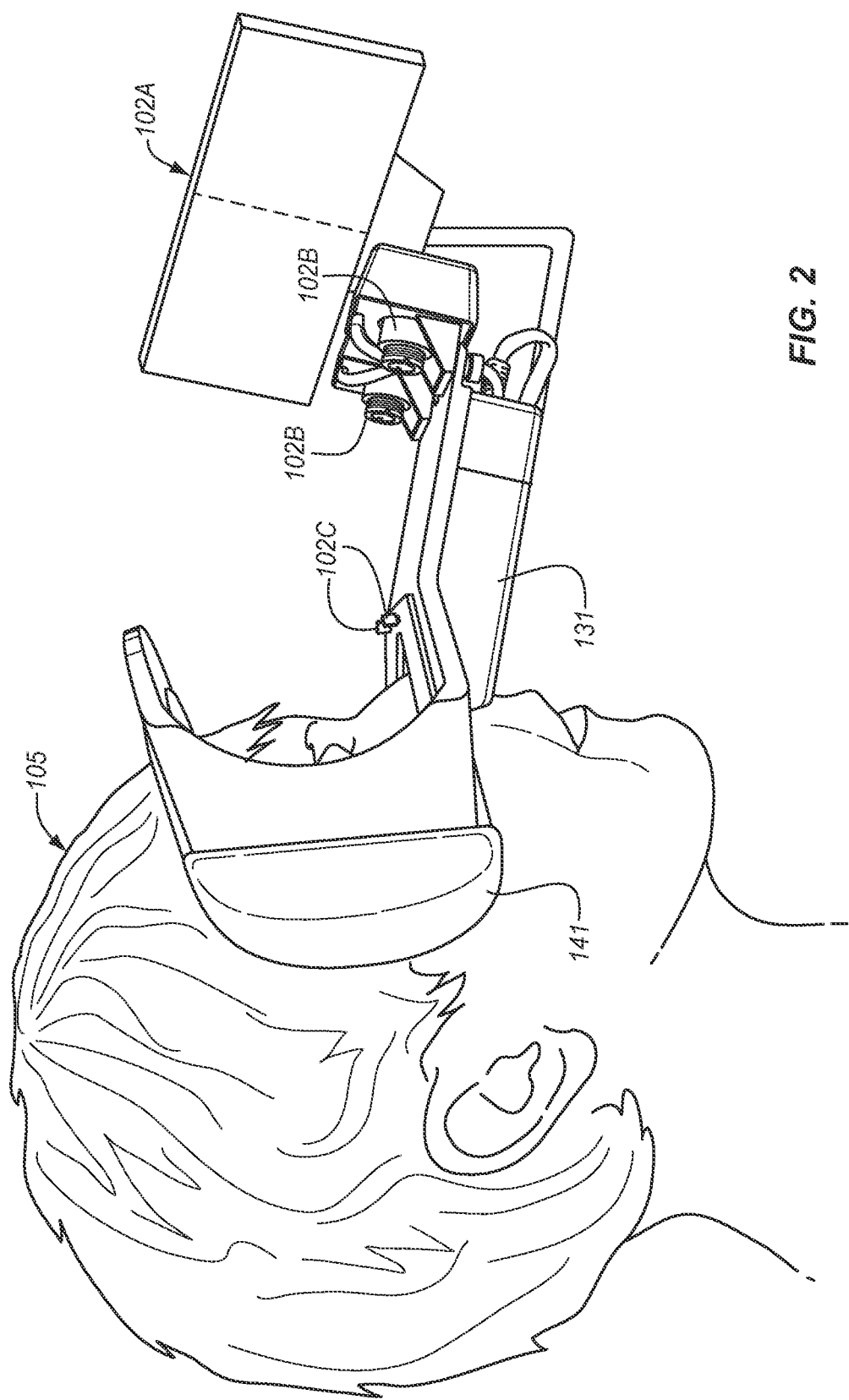
FIG. 2 illustrates a perspective view of an example of the apparatus of the OculoKinetic Device, where

The faceplate 141 illustrated in FIG. 2 positions the test subject's head with respect to Illumination Devices 102C and Ocular Measurement Devices 102B and also so the test subject 105 is looking at a Stimulus Presentation Display 102A. The faceplate 141 typically has two eye openings through which Illumination Devices 102C, attached to a frame 131, transmit beams of infrared light to illuminate the test subject's eyes. Two Ocular Measurement Devices 102B, also attached to frame 131, are mounted opposite the eye openings to generate images of the subject's illuminated eyes. The generated images are transmitted to an Image Recording Device 103F for storage and optionally to Display 101A (as shown in FIG. 1) for display to a test administrator. The test subject's ocular responses, including eye movement, pupil response, etc., are recorded.

The Ocular Measurement Devices 102B are connected to an Image Recording Device 103F with the capability of storing video images or video stream in digital format such as on a disk drive, USB flash drive, solid state drive, compact flash cards, other local or networked storage devices, or other such apparatus for capturing and storing image data. The interconnection between the Ocular Measurement Devices 102B and the Image Recording Device 103F can be wired or wireless, using a cable or wireless communication protocol, respectively. Using the OculoKinetic Device 100, the test subject 105 looks into the system at the Stimulus Presentation Display 102A, which presents ocular stimuli representative of previously defined tests, which may consist of (but are not limited to) any of the following test protocols or combination of these test protocols: (1) Smooth Pursuit, (2) Saccade, (3) Optokinetic, and (4) Pupillography. The test subject's eyes are tracked by the Ocular Measurement Devices 102B operating with Eye Movement Computation Process 103E sampling the generated images at a pre-selected sampling frequency, since the faster the sampling rate, the more accurate the data, and thus the resulting Waldorf Score (as described below). This sampling frequency is an important parameter, since aspects of the eye movements cannot be adequately assessed with slower scan frequencies. For instance, the acceleration/deceleration profile of the eye when performing a Saccade test, or the evaluation of the micro-saccades when fixating on a target that is stationary, or the speed of a blink, hippus, or pupil oscillations, etc., occur at a rapid rate, which requires a higher sampling frequency for accurate detection and quantification.

Beam-splitter lenses also can be used, thereby allowing the Ocular Measurement Devices 102B to track the eyes while the test subject 105 is looking at the Stimulus Presentation Display 102A if the cameras are located outside of the "line of sight." Other embodiments could be one Ocular Measurement Device 102B looking at both eyes at the same time, one Ocular Measurement Device 102B which sequentially looks at one eye and then the other, or just one Ocular Measurement Device 102B tracking the eye movements of a single eye. Apropos to this Ocular Measurement Devices/eye group of configurations would be the eye/Stimulus Presentation Display 102A arrangement. This could range from a one eye-one Stimulus Presentation Display 102A configuration, to one that allowed both eyes at the same time to view a target on the Stimulus Presentation Display 102A, to a situation where one eye sees one Stimulus Presentation Display 102A or part thereof and the other eye sees another Stimulus Presentation Display 102A or part thereof. In this last configuration, it could be that the right eye would never see what is being presented to the left eye because of an internal divider that would preclude this cross eye/target ability.

One of the preferred embodiments of the Stimulus Presentation Display 102A is to use existing flexible display technology to totally wrap the Stimulus Presentation Display 102A within the internal field of view of the enclosure 104 (wrap-around display). The benefits of this configuration include:

High Reliability—Environmentally friendly construction with long and safe operation in the most demanding of operational environments;

Optimal Full-Field Visibility—Excellent display characteristics even when viewed from extreme angles and in less than optimum conditions; and Enhanced Viewability—Continuous improvement in design and manufacture in order to achieve display of true-to-life images.

Calibration, Sampling, and Analysis

Magnification

Figure 9:
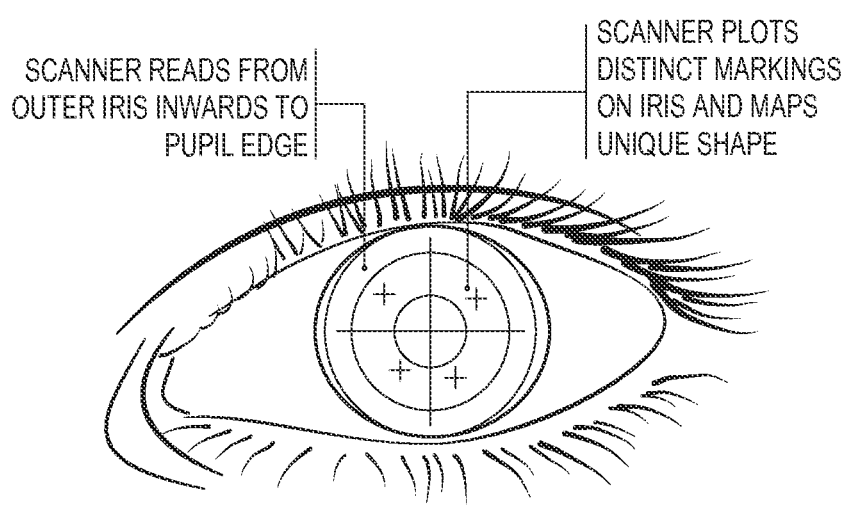
FIG. 9 is a drawing illustrative of a typical iris biometric identification measurement used in the OculoKinetic Device.
Figure 11:
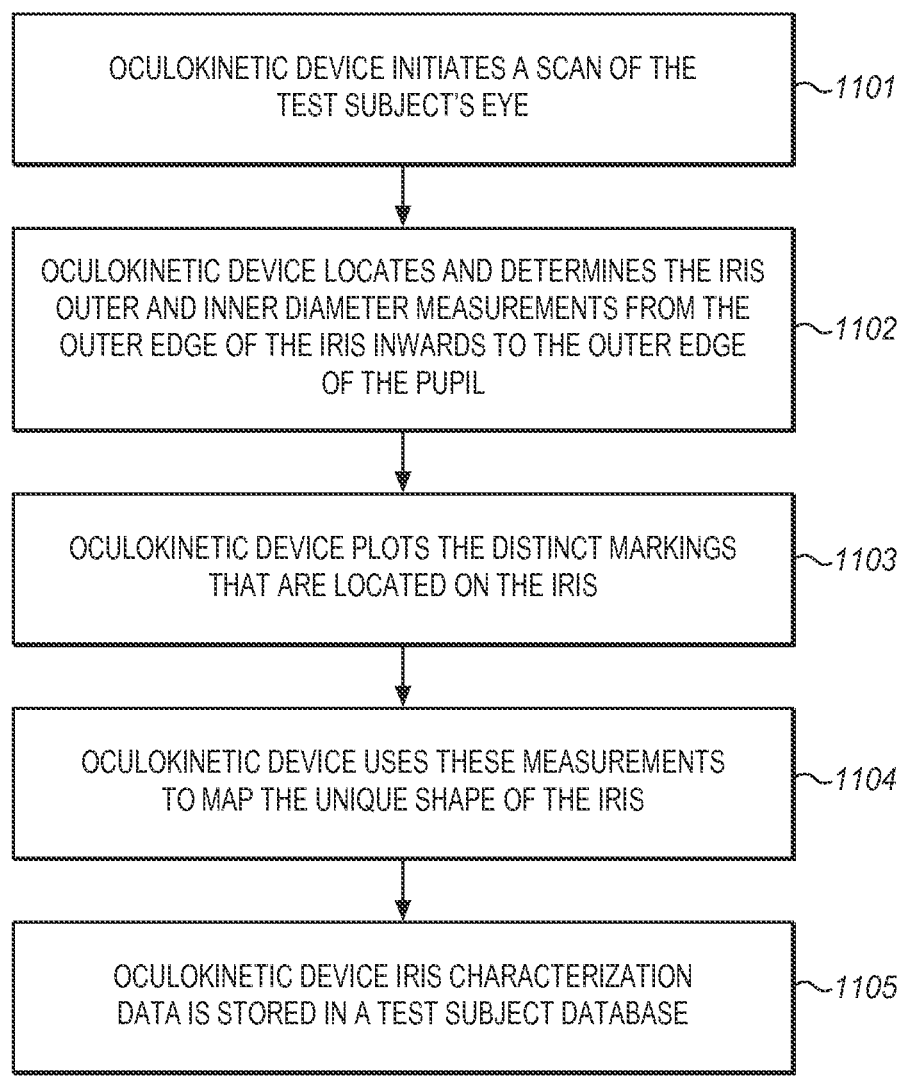

Knowing the actual size of the pupil 801, as shown in FIG. 8, is important from the standpoint of determining its centroid for position analysis, i.e., the size leads to a computation of the pupil's center giving an X, Y coordinate. It is the change in this X, Y coordinate over time that results in the digital description of the movement of the eye, i.e., left-right, up-down. It is also important in determining the location and size of the iris (see below) which can be used to analyze the torsional movement of the eye and also as a biometric identifier (also discussed below). Since the size of the pupil can change based on many factors, i.e., ambient light, medications, injury, etc., knowing a stable parameter would greatly assist in any resulting pupil size metric. The iris 802 of the eye 803 is a stable parameter that does not change size. Thus, the diameter of the iris 802 can be used in a mathematical ratio with the pupil size to provide a more accurate assessment of the pupil's true size. For example, if the true size of a subject's iris diameter is 20 mm, one could use that number each time that particular test subject is tested to establish the change in the magnification factor for any subsequent test of that particular test subject. If a subsequent test showed the iris diameter to be 15 mm, it would be known that the test subject's head was slightly farther away from the camera than the baseline test. The computer analysis of the pupil size would be compensated by this difference. FIG. 9 is a drawing illustrative of typical pupil calibration measurements used in the OculoKinetic Device 100, and FIG. 11 illustrates the steps taken to compute the iris measurement, as is described below. Pupil measurements are well known, and U.S. Pat. No. 7,614,745 teaches a system for such measurements.

To increase the accuracy of the eye tracking, the disclosed technique determines the magnification factor underlying digital eye tracking (infrared and/or visible illumination) by using the diameter of the iris/sclera border as a constant to which all other tests of that same test subject are calibrated. As this border does not significantly change in size from puberty through adulthood, it provides an ideal metric for determining how close or far a test subject's eye is from a digital sensor (magnification factor). By knowing this factor, the system can automatically adjust for any changes in the magnification factor. This method of using the iris-sclera boundary size (diameter, radius, circumference, etc.) enhances the accuracy of the detection of eye movements, i.e., eye tracking, pupil size and reactivity determinations, iris location and size, etc.

The OculoKinetic Device 100 maps the unique characteristics of the iris 802 and determines a magnification factor by scanning the eye to detect the outer edge of the iris 802. By identifying the outer edge of the iris 802, its unique shape can be mapped and its size determined FIG. 11 illustrates, in flow diagram form, the operation of the OculoKinetic Device 100 to identify unique iris characteristics. A scanner at step 1101 initiates a scan of the test subject's eye(s) 803 and, at step 1102, locates and determines the iris outer and inner diameter measurements from the outer edge of the iris 802 inwards to the outer edge of the pupil 801. The scanner also plots, at step 1103, the distinct markings that are located on the iris 802 and, using these measurements, maps the unique shape of the iris 802 at step 1104. After plotting the iris markings and shape, the significant iris characterization data is stored in a database at step 1105.

Using the size of two images of the iris 802 to determine a magnification factor has not been previously used in eye tracking and any other pupillography techniques (ultrasound, radio-frequency technology, etc.). In addition to the iris size metric for adjusting the magnification factor, the addition of iris identification to a system that is already configured for digital eye tracking increases the utilitarian aspect of a product.

An embodiment is an automatic, software-controlled feature which does the comparison of a current test result to that of a prior result (i.e., baseline, sequential past tests, forward-looking comparisons of current test to future tests, etc.). Further, it is claimed that this enhanced ocular system can be used for various discrete and defined applications such as the screening and evaluation of brain function related to concussions/head injury, medical videonystagmographic (VNG) testing, pupillography, etc.

Test Subject Identification

The OculoKinetic Device 100 may also use the eye as a biometric for the identification of the individual being tested, as shown in FIG. 8, since the striation pattern 805 in the iris 802 of the eye 803 is an immutable physical characteristic unique to each test subject—even to the level of the differences between the same subject's right eye iris patterns from their left eye iris patterns. This may assist in the protection issues of human data as names, etc., would not be required, i.e., HIPAA compliant de-identifiable data. Identification using iris landmarks, or striations, is an existing technology, but not one that is seen in medical eye tracking devices. Being able to use the biometric of "iris identification" for identifying the test subject as well as a means to retrieve prior subject data for any comparison analysis—without the need for operator control of that function—in an eye tracking system is unique.

The iris 802 with its complex texture has been proven to make a reliable biometric recognition method. The iris 802 is an annular area between the pupil 801 and the white sclera 804 in the eye 803. Its complex pattern contains many distinctive features such as arching ligaments, crypts, radial furrows, pigment frill, papillary area, ciliary area, rings, corona, freckles, and zigzag collarets which provide a unique set of characteristics for each human being; even the irises of identical twins are different.

Data Processor 103 compares the presently generated set of iris characteristics that are unique to the test subject with the retrieved previously generated set of iris characteristics that are unique to the test subject. The Data Processor 103 authenticates the identity of the test subject in response to the presently generated set of iris characteristics that are unique to the test subject corresponding to the retrieved previously generated set of iris characteristics that are unique to the test subject.

Various Test Protocols

Existing standard-of-care eye movement stimulus protocols include, but are not limited to:

1. Smooth Pursuit—tracking eye movement that follows movement of a target in a horizontal direction or movement of a target in a vertical direction.
2. Gaze—gaze-induced nystagmus occurs or is exacerbated as a result of changing one's gaze toward or away from a particular direction.
3. Saccade—tracking quick, simultaneous movements of both eyes in the same direction. The saccade target is usually presented either horizontally or vertically.
4. Optokinetic—The standard optokinetic stimulus is a series of stripes that can be moved either horizontally or vertically.

The nature of the existing equipment that produces these stimulus protocols, i.e., discrete light bars, dots on the wall, etc., test eye responses exclusively in the horizontal direction or exclusively in the vertical direction. This is limiting to a complete eye movement examination, since the eye has three pairs of eye muscles, each being controlled by a separate set of brainstem nuclei and neural pathways which allow the eye to move in any direction in a two-dimensional plane, including torsional eye movements, i.e., those about the visual axis.

In contrast, the OculoKinetic Device is able not only to do this "limited" testing but, in addition, has the capabilities to produce eye movement stimuli that move in any direction in a two- or even a three-dimensional plane. For example, with a Smooth Pursuit test, instead of a target moving horizontally only or vertically only, it may move in a FIG. 8 pattern or a more complex, randomized pattern. The OculoKinetic Device test protocols also are not limited to just black and white images, but can include visual targets that may increase the accuracy of evaluating brain function by using colored dots, stripes, etc. In addition, the use of symbols is anticipated, where the ocular stimuli are geometric shapes, multi-colored images, flashing images, etc. Such diversity in target presentations are beneficial in the testing of younger athletes and children who are more inclined to look at and follow shapes and colors rather than just black and white dots or lines.

In addition, these types of "eye-catching" stimuli can be used in conjunction with cognitive testing. As one of many possibilities, the Saccade test could be done with dots of a certain color. The test subject is instructed to look only at blue dots. Some of the dots would be presented in blue, but others could be red, yellow, etc. By seeing how the test subject's eye(s) move(s) or fail(s) to move from colored dot to colored dot, and analyzing the "errors," a more accurate neuro-cognitive test of possible brain trauma may be established.

Finally, the eye movement protocol results, optionally coupled with results from other non-eye tests, i.e., balance, information from a physical exam, etc., can be used to compute a metric termed herein the "Waldorf Score," which scales the brain injury of the subject by incorporating a plurality of measured metrics. It is computed from the results of the various oculomotor tests at a minimum, ranging to a compilation of data such as, but not limited to, pupillography, balance test results, cognitive test results, plus metrics such as blood pressure, body temperature, etc., which can be taken from the eyeball. By knowing the "Waldorf Score" for a test subject at any point in time provides clinicians and other interested parties the ability to more easily understand the neurophysiological status of the central nervous system.

Figure 3:
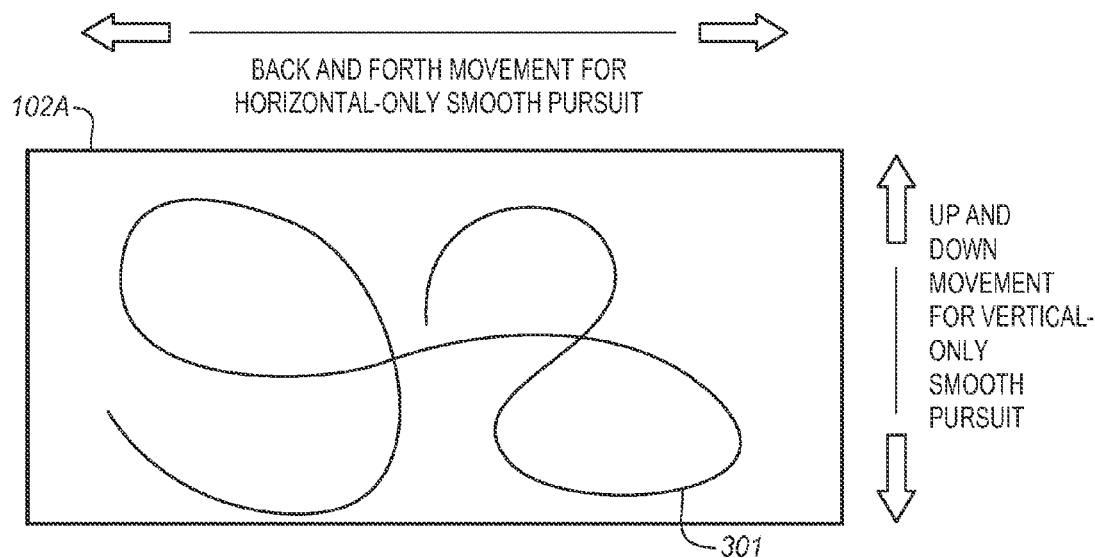
FIG. 3 is a drawing illustrative of a Smooth Pursuit image display which can be used in the OculoKinetic Device.

There are several existing eye movement stimulus test protocols 103A (as in FIG. 1) or other types of tests that may be used for the application of defining brain functionality. They are:

1. Smooth Pursuit—a task in which the test subject is asked to keep their head still and track a moving object (sometimes referred to as "eye tracking"). FIG. 3 is a drawing illustrative of a typical Smooth Pursuit image 301 display used in the OculoKinetic Device 100. Existing Smooth Pursuit stimulations consist of only horizontal target movements or vertical target movements. There have been published smooth pursuit paradigms that are circular in nature, i.e., follow a moving target that circumscribes a circular path.

2. Free-Form type of paradigm—the analysis of the response is to see how well the test subject is able to track the moving target, i.e., accuracy of staying within certain defined standard deviations which may change depending on a test subject's age or other indications. The target may move at a stable speed, or may have accelerations/decelerations, color changes, target sizes, etc. The size of the area involved in the total smooth pursuit area of view may be changed as well.

Figure 4:
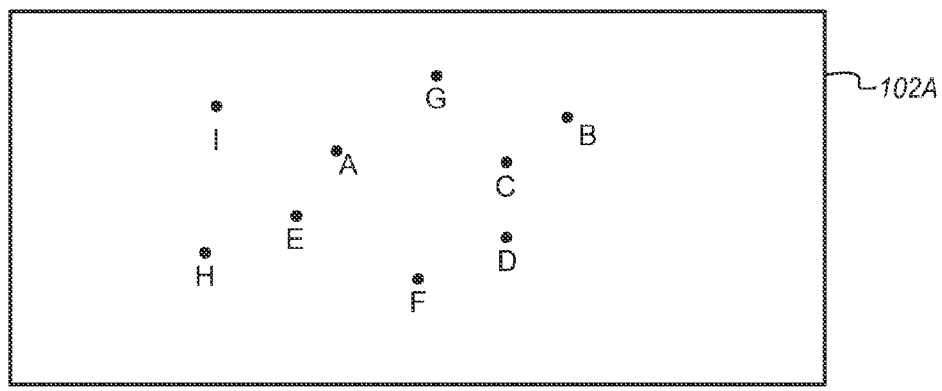
FIG. 4 is a drawing illustrative of a Saccade image display which can be used in the OculoKinetic Device.

3. Saccade—A saccade is a fast movement of the eye. Saccades are quick, simultaneous movements of both eyes in the same direction in people who have normal brain functional control of the oculomotor system. The saccade target usually is presented either horizontally or vertically. As with the OculoKinetic Device Smooth Pursuit paradigm, a more complex stimulus is being claimed, one that may look like the multi-point (A-I) stimulus illustrated in FIG. 4, or any other degree of complexity.

In this case, the test subject would start looking at the target in the "A" position. At some time, the "A" target disappears and the "B" target at that same time becomes visible. The analysis is done on the latency for the eye to begin its movement from "A" to "B"; how long it takes the eye to get to "B"; whether the acceleration and velocity profiles within the test subject's and/or population normative values; and does the eye stop at "B," does it stop before "B" (called an "undershoot"), or does it pass "B" (called an "overshoot"). Both of these latter conditions then require the eye to do a corrective eye movement to get to the "B" target.

One of the reasons for the above-noted requirement of high speed is to have a sufficient number of sampling points of the movement of the eye to get an accurate assessment of the acceleration/deceleration profiles, as well as any corrective eye movement responses because of the undershoot/overshoot phenomenon. In addition, the high speed allows for a comparison of the alignment, movements and acceleration/deceleration profiles of one eye to the other in the same test subject.

The Saccade test can incorporate changes in target colors, shapes, etc., which would bring a unique "cognitive" function to the standard Saccade protocol. For instance, the test subject may be asked to look only at red target lights. "A" would be red, and let's say "B" is red as well, but "C" may be green. The test administrator would want to see if the test subject knows not to look at "C." If the test subject does start to make the eye movement to "C," how long does it take the test subject to stop their eye movement, etc.? This combination of standard eye movement tests coupled with cognitive tasks is a unique enhancement to the science of defining brain functionality.

Figure 5:
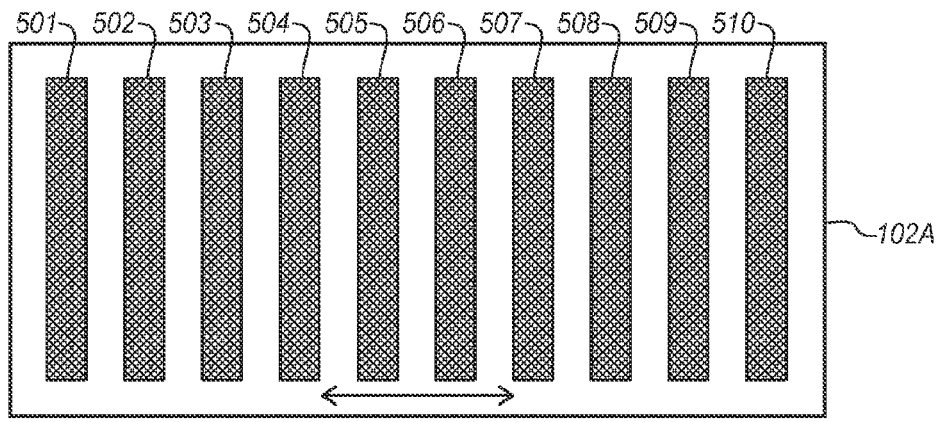
FIG. 5 is a drawing illustrative of an Optokinetic image display which can be used in the OculoKinetic Device.

4. Optokinetic (OPK)—The optokinetic reflex allows the eye to follow objects in motion when the test subject's head remains stationary (e.g., observing individual telephone poles on the side of the road as one travels by them in a car). FIG. 5 is a drawing illustrative of the standard Optokinetic image display where, for horizontal OPK stimulation, the entire field of view is populated with stripes 501-510 aligned in a vertical direction and the stripes move in unison to the right or to the left. This same protocol is used for vertical OPK stimulation, where the stripes are aligned in a horizontal direction and they move in unison up or down.

OculoKinetic Device Test Protocol

The ocular response characteristics are based on the target stimuli being presented, and all are based on current conventional methods for reporting such results. As an example, a Smooth Pursuit test plots like a moving sinusoidal wave pattern. The eye tracking results computed by the Eye Movement Computation Process 103E would be compared to the stimulus pattern (as stored in Test Protocols 103A) in terms of parameters that can include phase and gain. As an example, the phase and gain numbers then are compared by the Data Processor 103 to one or more selected data sets in the Normative Database 103B, such as population norm, the individual norm, a combination of both, etc. For Saccade results, the eye tracking wave form is compared to that of the visual stimulus contained in the selected test protocol. In this case, an important test result is latency, i.e., how long after the target light has gone from point "A" to point "B" does the eye make its move to point "B"? The Test Subject Stimulus Response Process 103C then looks at issues related to the acceleration, deceleration, and velocity of the eye movement. Finally, the accuracy of the test subject's eye directly stopping at point "B" is a significant metric. In many cases of brain injury, this can be a negative accuracy or undershoot where the eye stops before point "B" and then does a reflexive "catch-up" movement, or it can be a negative accuracy or overshoot where the eye goes past point "B" and then does a reflexive "back-up" movement to the target. For Optokinetic stimulations, the speed of the eye is measured in tracking the speed of the moving stripes, and then the automatic reverse Saccade when the eye can no longer physically move in the direction of the moving stripes. In this case, the eye should move with the stripes at the speed they are moving, with the corrective Saccade having its own characteristic of acceleration and velocity. Again, these results can be compared to a population norm and/or the test subject's normative baseline values.

What is unique about the Optokinetic test implemented in the present OculoKinetic Device is that it encompasses both Smooth Pursuit as well as discontinuous patterns, such as Saccade eye movements. For example, if the stripes are moving to the right, the eye follows a stripe until the eye can no longer physically move right (the Smooth Pursuit part of the Optokinetic stimulus). The eye then does a corrective Saccade to the left to find another stripe. It then follows that rightward moving stripe and so on. The Test Subject Stimulus Response Process analysis compares the movement of the eye during the smooth pursuit stage to the speed of the movement of the stripes. It also determines the speed of the corrective Saccade (velocity and acceleration profiles). As with the other eye movement tests described above, and related to the claim of intra-personal baseline comparisons, how well a test subject does this (these) task(s) may be compared to their ability to have accomplished the same prior to any head injury/ concussion, etc. In addition, the OculoKinetic Device 100 may use a protocol that includes moving the stripes in an oblique direction from lower left to upper right, upper right to lower left, and any other paths that are angularly displaced from the horizontal and vertical axes.

Figure 6:
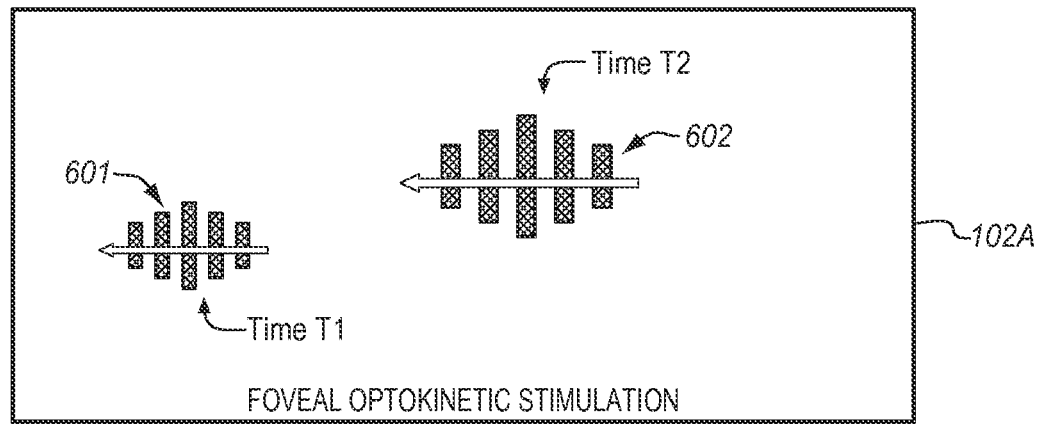
FIG. 6 is a drawing illustrative of a Foveal Optokinetic image display which can be used in the OculoKinetic Device.

The OculoKinetic Device 100 may implement a new paradigm of VNG testing: Foveal and Peripheral OPK testing. Because the OculoKinetic Device 100 uses high speed video sampling rates for knowing the eye position, it can use the instantaneous eye position to control the placement of the stimuli. In the case of Optokinetic stimuli, these two additional types of stimulations are used in addition to the full field Optokinetic test:

Foveal OPK: The moving pattern of stripes is only present in an area of interest that follows the direct line of sight of the test subject. In FIG. 6, you see the moving stripe pattern 601 at Time T1 and the field of view of the moving OPK stripes. At Time T2, the eye has to move to a new location (602); and the area of interest of the OPK moving stripes moves as well. Thus, only the Foveal part of the retina is stimulated by this protocol.

Figure 7:
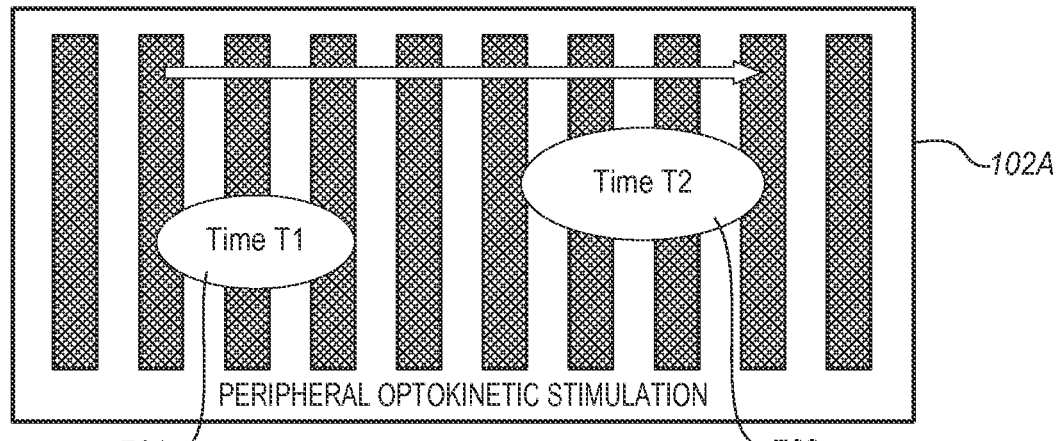
FIG. 7 is a drawing illustrative of a Peripheral Optokinetic image display which can be used in the OculoKinetic Device.

Peripheral OPK: This is just the opposite of Foveal OPK. As shown in FIG. 7, Peripheral OPK stripes are only displayed outside the area of direct vision 701, 702.

Present stimuli used in optical testing are presented in a two-dimensional plane; however, one of the embodiments of the OculoKinetic Device 100 has the capability to expand that, when desired, to a three-dimensional presentation, i.e., imagine looking at a target dot that moves to the right, left, up, down, and/or in an oblique manner. Now add to that the fact that the target dot can be made, at times, to come closer to the subject, i.e., gets larger, or moves farther away by getting smaller (with the parallax that is required for three-dimensional viewing—one eye sees the target in a slightly different position than the other eye, and the brain arranges these two slightly different images to mean depth. Using existing technology, this function is present in the OculoKinetic Device 100.

Color-Based Optokinetic Stimulus

A color-based cognitive feature is contemplated for use with the Optokinetic stimulus, where the test subject is told to only look at a red stripe which may be amongst different colored stripes. This and the other stimulations, including background colors, target colors, shapes, etc., can be changed—and these changes may allow for a more age-defined test, i.e., children may find it easier to track a "Smiley Face" rather than just a target dot.

The underlying reason for having these types of Optokinetic stimulations is the fact that it is different neural pathways within the brainstem that control this ocular reflex. The goal is to test as many of the neural pathways in an age-independent manner that might be affected by head trauma/concussion, since it remains an unknown at this time which of the target stimulations or combination thereof yields the most accurate results for the intended application.

Additional Physiological Measurements

Pupillography includes the recording of pupillary responses of the eye. The novelty of this testing is combining it with the eye movement tests which adds to the validity of the resulting "Waldorf Scale" of brain status. Although inherent in most video-based eye tracking is the ability to know the pupil information, the novel use of combining that information with the eye tracking and/or other ocular parameters is novel.

Measurements may include, but are not be limited to:

Pupil Size

Pupil reaction to light stimulation, such as time to react, time to maximum constriction, rebound dilation, average size during illumination, etc.

Hippus (oscillations of the pupil that are inherent in its normal functionality)

Cognition—The mental process of knowing, including aspects such as awareness, perception, reasoning, and judgment. As mentioned in several of the eye stimulation paradigms above, the combination of having the test subject perform (or not perform) a task while the eye is being stimulated is claimed to be an important construct of the OculoKinetic Device, especially as combined with eye tracking tasks.

Blinks—the high speed requirement for scanning allows for the discrete analysis of the blink frequency, as well as issues related to the speed of the blink, the time of eye closure, etc., even the evaluation of the "dolls eye" phenomenon where eyes roll upwards as the upper eyelid comes down.

Ptosis—This is a "droopy" eyelid. It is anticipated that some injuries may result in an eyelid that does not open as much as in the pre-injury condition. This is determined from the eye tracking algorithms that compute the size of the pupil (see discussion below). A droopy eyelid, as captured digitally from the OculoKinetic Device, may be part of the "Waldorf Score" computation.

"Waldorf Score"

Finally, the eye movement protocol results, optionally coupled with results from other non-eye movement tests, i.e., neurocognitive and balance testing, information from a physical exam, etc., can be used to generate a metric termed herein the "Waldorf Score," which scales the brain injury of the subject by incorporating a plurality of measured metrics. It is computed from the results of the various oculomotor tests at a minimum, ranging to a compilation of data including, but not limited to, pupillography, balance, and cognitive test results, plus metrics such as blood pressure, body temperature, etc., which can be taken from the eyeball. On-going research and/or data mining provide the various analytical "weights" or importance of any individual parameter used in the "Waldorf Score." Just an example of the possibilities could be the correlation that concussions always produce issues with the eyes being able to track a moving target, and this becomes more significant as pupil reactivity is changed from normal and the blink rate is slowed. By combining these three elements (in this example with equal weight/significance), the "Waldorf Score" becomes a more robust, statistically significant result.

Furthermore, it is contemplated that the "Waldorf Score" itself may have various levels of sensitivity depending on the application, i.e., a "Basic Waldorf Score," which is based solely on the results from the oculomotor tests and pupillography; an "Enhanced Waldorf Score," based on the parameters of the Basic Waldorf Score plus the results of balance testing protocols; and the "Ultra Waldorf Score," which includes the Enhanced Waldorf Score data plus the results of neurocognitive test protocols and physical and physiological examinations.

Knowing the "Waldorf Score" for a patient at any point in time provides clinicians and caregivers the ability to more easily understand the neurophysiological issues at play in determining brain status and function, and guide therapeutic and rehabilitation programs, as well as assist in making "return to play" or "return to duty" determinations.

To monitor the movements of the patient's eyes, ocular measurement devices that are sensitive in the near infrared illumination spectrum, or using wave front technology, etc., are positioned in the field of vision of the test subject to record their eye movements during testing. These ocular measurement devices are housed in a test subject interface—which can be in the form of goggles, head-mounted configurations, or positioned in a "dedicated tunnel" or "cone of darkness" viewport-type device—as a means of eliminating ambient light from impinging on the eye. In addition, a stimulus presentation device is included in the test subject interface to display visual stimuli for the test subject. To maximize the efficacy of these measurements, it is imperative that the configuration of the ocular measurement devices, the stimulus presentation device, and the test subject be arranged in a manner that controls the ambient light impinging on the test subject's eyes, as well as the elimination of extraneous visual targets from the test subject's field of vision. All of this must be accomplished in an ergonomically sound and reproducible manner such that the test subject can easily be tested in a quick and efficient manner on, in, or adjacent to a field of play, combat zone, or industrial environment.

The ideal system for the physiologic evaluation of brain function has the following features: self-diagnostics to ensure each test is being performed with the electronics and software working at their optimum; ability to document the test subject, stimulus paradigms, and test results in a manner that meets the requirements for human subject medical applications; and it must meet the criterion for functional testing in ambient environments that are variable in terms of weather, temperature, and other testing environment constraints. A numerical output is essential for accurate comparison to normal subjects, the patient's own normative baseline score, and progression or deterioration of their condition over time.

The "Waldorf Score" is a numerical output, for example on a scale of 0-100, which provides an indication of the level of brain functionality based on the results of the tests performed by the OculoKinetic Device. This score optionally includes data other than data generated by the test controller 102 of the OculoKinetic Device 100, i.e., results from balance and neurocognitive tests, medical history, physical examination, vital signs, etc. Also, issues related to the mTBI injury (sports activity, running into a stationary object, being hit by a moving object, acceleration and direction of the head insult, etc.) can be input as factors that can be used in determining a score for the potential mTBI. The "Waldorf Score," when used for issues related to head trauma/concussion from sports injuries, is part of the immediate decision made at the point/time of injury, as well as in the post-injury/concussion treatment process and rehabilitation related to what is referred to as the "decision for Return to Play." Thus, the "Waldorf Score" for any person may go from 100, meaning totally normal brain function, to a 65 at the time of injury, and then up to a 75 two weeks later after medical intervention, rest, etc., and progressing to an 85, which may be the level that allows for the decision for a patient to Return to Play. These are hypothetical values but represent the concept underlying the use of the "Waldorf Score."

Operation of the OculoKinetic Device

Figure 10A:
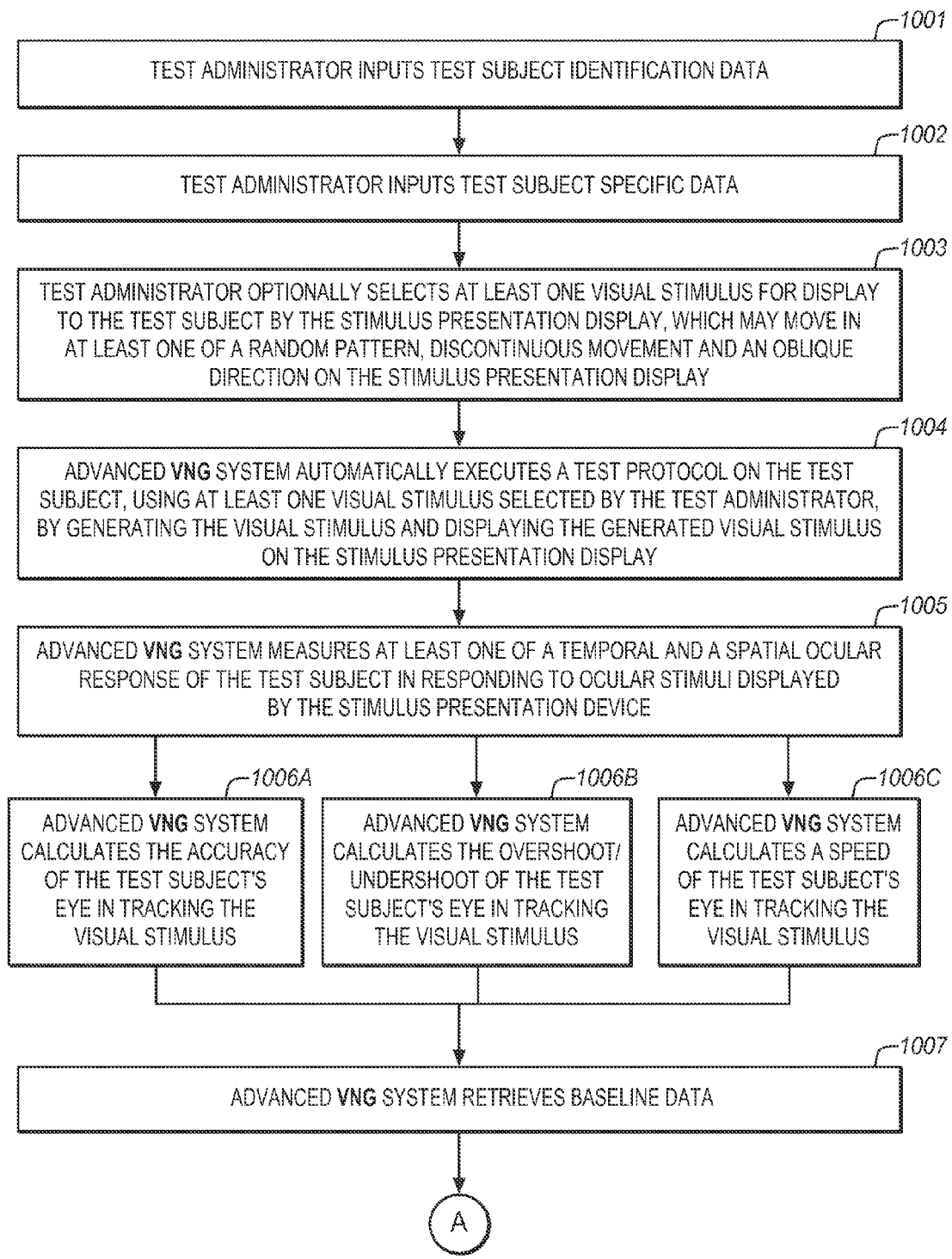
FIGS. 10A, 10B, and 11 illustrate, in flow diagram form, one possible embodiment of the operation of the OculoKinetic Device.
Figure 10B:
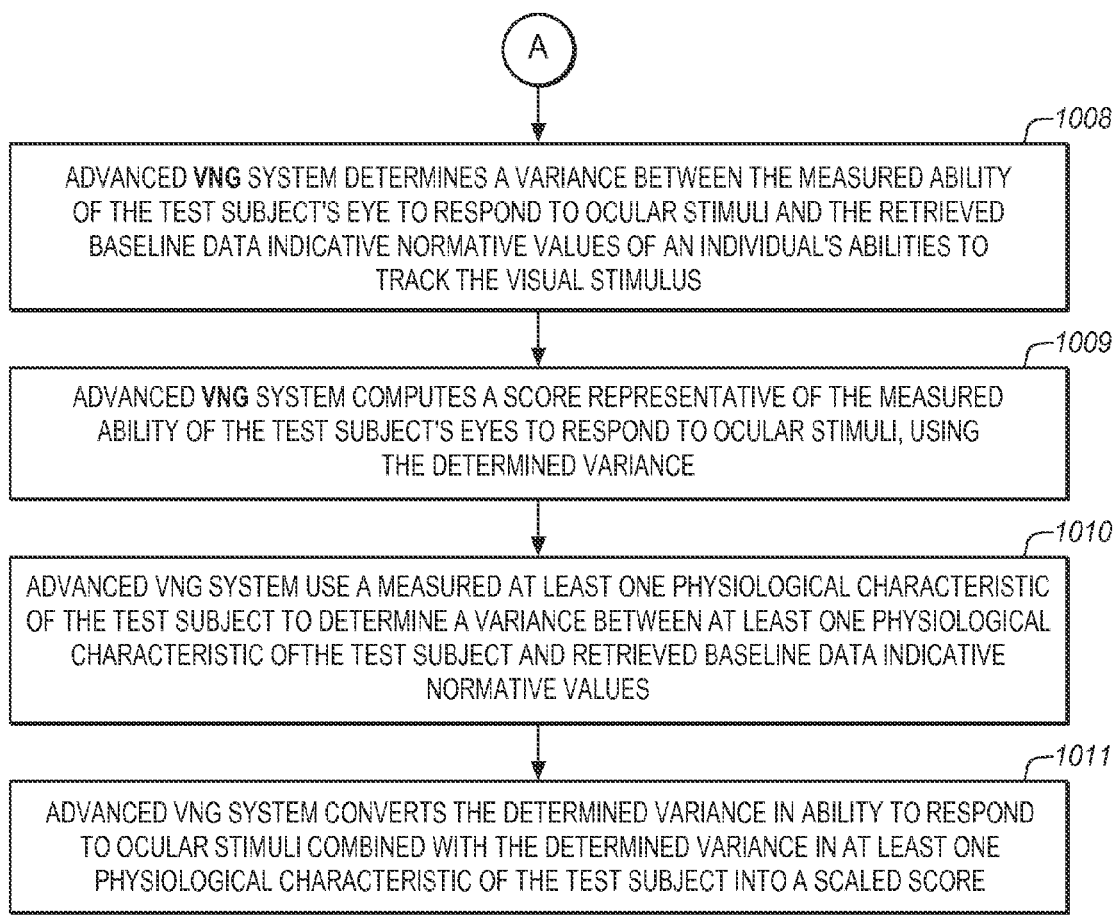

FIGS. 10A and 10B illustrate, in flow diagram form, the operation of the OculoKinetic Device 100 in executing an exemplary test or series of tests on a test subject to measure the ability of the test subject's eyes to track a visual stimulus. An analogous set of tests can be conducted to measure the pupillary responses of the test subject to stimuli but, for the sake of simplicity, the target tracking example is used herein. At step 1001, the test administrator activates the OculoKinetic Device 100 and inputs test subject identification data into the Data Input Interface 101B to uniquely identify this test subject and thereby create a file in the Data Processor 103 associated with this test subject. At step 1002, the test administrator inputs, via the Data Input Interface 101B, test subject specific data, such as: age, sex, nature of possible injury, and optionally at least one physiological characteristic of the test subject selected from the set of physiological characteristics including: pupillography, cognition, balance test results, cognitive test results, blood pressure, body temperature, etc. At step 1003, the test administrator optionally selects at least one visual stimulus for display to the test subject by the stimulus presentation display which moves in at least one of several possibilities including, but not limited to: a random pattern, discontinuous movement, and an oblique direction on the stimulus presentation display.

At step 1004, the OculoKinetic Device 100 automatically executes a test protocol on the test subject, using the at least one visual stimulus selected by the test administrator, by generating the visual stimulus and displaying the generated visual stimulus on the Stimulus Presentation Display 102A. The OculoKinetic Device 100 may include automated verbal instructions to the subject instead of a test administrator giving instructions. At step 1005, the OculoKinetic Device 100 measures, using the ocular measurement device, at least one of a temporal and one of a spatial eye movement of the test subject in tracking the visual stimulus displayed by the stimulus presentation device. At steps 1006A-1006C, the OculoKinetic Device 100 automatically performs at least one analysis determination and calculates a speed of the test subject's eye in tracking movement of the visual stimulus, and/or calculates the accuracy of the test subject's eye in tracking movement of the visual stimulus, and/or calculates the overshoot/undershoot of the test subject's eye in tracking movement of the visual stimulus, respectively. At step 1007, the OculoKinetic Device 100 retrieves baseline data indicative of an individual's abilities to track the visual stimulus from a normative database and, at step 1008, determines a variance between the measured ability of the test subject's eyes to track the visual stimulus and the retrieved baseline data indicative normative values of an individual's abilities to track the visual stimulus. At step 1009, the OculoKinetic Device 100 computes a score representative of the measured ability of the test subject's eyes to track the visual stimulus, using the determined variance for display to the test administrator.

In addition, the OculoKinetic Device 100 at step 1010 optionally can use a measure of at least one or more physiological characteristics of the test subject selected from a set of physiological measures including, but not limited to: pupillography, cognition, balance test results, cognitive test results, blood pressure, and/or body temperature to determine variances between the chosen physiological characteristic(s) of the test subject and the retrieved baseline data from that same individual and/or a population norm for that same data set of measures. At step 1011, the OculoKinetic Device 100 converts the determined variance in ability to track the visual stimulus combined with the determined variance in at least one physiological characteristic of the test subject into a scaled score for display to the test administrator.

Baseline and Data Mining

Some of the data in the public domain shows eye movement results in relationship to normative data, i.e., people of the same age with no head trauma tested with the same equipment in the same protocol, or against existing norms from other published studies that may or may not have used the same equipment. Testing an individual against their own baseline responses is a more accurate approach. One could contemplate that an individual may go through several rounds of testing on an OculoKinetic Device, i.e., before the season starts for a sport, at random times during the season, possibly before and after each game or match (boxing and football come to mind) The baseline data, therefore, would continue to be refined for that individual since human physiology is rarely constant. This is useful for data mining, since it is conceivable that an OculoKinetic Device 100 could be used in a high school football setting, for example; and as the individual progresses to college and professional sports, the data mining that may be included in the system software would create a valuable historical view of not only the individual's brain function but would add depth to any population norm that may evolve from this unique process. One method of transmission of this data would be to have subject de-identified (HIPAA compliant) data uploaded continuously to an Internet-based managed database, i.e., the "Cloud," and stored for later analysis.

The use of an individual's baseline test results is facilitated by the provision of the Test Subject Database 103B which stores the test results that were previously generated when the test subject was initially and/or most recently tested, using the OculoKinetic Device 100. By limiting the variability of the test procedure and test equipment, any differences in test results that are identified can be correlated with the measured physiological characteristic of the test subject.

Summary

The present OculoKinetic Device produces an eye movement stimulus protocol that moves in any direction of the two-dimensional or three-dimensional plane, including a more complex randomized pattern. The OculoKinetic Device test protocols also are not limited to just black and white images. It is conceivable that brain injury is more accurately detected by using colored dots, stripes, etc. In addition, the use of symbols is anticipated, where the ocular stimuli are geometric shapes, multi-colored images, flashing images, etc.

What is claimed:

1. A method for computing a measure of the ocular response of a test subject, in response to predetermined stimuli, which are presented on a stimulus presentation display that can be viewed by the eyes of the test subject, for viewing by the test subject, comprising:

generating a stimulus including visual target movement in at least one of: a random pattern, a discontinuous movement, and an oblique direction on the stimulus presentation display, for display to the test subject;

measuring, using an ocular measurement device, at least one of a temporal eye movement, a spatial eye movement, pupil size, and pupil reactivity of the test subject in responding to the visual stimulus presently displayed by the stimulus presentation device; and computing a score representative of at least one of the measured ability of the test subject's eyes to track the visual stimulus and the measured pupillary metrics of the test subject's eyes, comprising:

scanning an iris of the test subject to generate a present set of iris characteristics that are unique to the test subject;

retrieving from a test subject database baseline data comprising a previously generated set of iris characteristics that are unique to the test subject;

determining a variance between the presently generated set of iris characteristics that are unique to the test subject and the retrieved baseline data comprising the previously generated set of iris characteristics that are unique to the test subject;

authenticating, in response to the presently generated set of iris characteristics that are unique to the test subject corresponding to the retrieved previously generated set of iris characteristics that are unique to the test subject, the identity of the test subject;

retrieving baseline data, indicative of the test subject's previously measured ocular responses, from a database; and determining a variance between the presently measured ability of the test subject's ocular responses and the retrieved baseline data indicative of the test subject's previously measured ocular responses.

2. The method of computing a measure of the ocular response of a test subject of claim 1, further comprising:

storing the presently generated set of iris characteristics that are unique to the test subject in the test subject database.

3. The method of computing a measure of the ocular response of a test subject of claim 1 wherein the step of scanning comprises:

mapping the striations of the test subject's iris; and plotting these distinct iris markings located on the test subject's iris.

4. The method of computing a measure of the ocular response of a test subject of claim 3, further comprising:

storing the presently captured data of the test subject's iris and the plotted distinct iris markings located on the test subject's iris in the test subject database.

5. The method of computing a measure of the ocular response of a test subject of claim 1 wherein the step of measuring comprises:

calculating a speed, which may include rates of change of velocity, of the test subject's eye in tracking movement of the visual stimulus.

6. The method of computing a measure of the ocular response of a test subject of claim 1 wherein the step of measuring comprises:

calculating the accuracy of the test subject's eye in tracking movement of the visual stimulus.

7. The method of computing a measure of the ocular response of a test subject of claim 1 wherein the step of measuring comprises:

calculating the overshoot/undershoot of the test subject's eye in tracking movement of the visual stimulus.

8. The method of computing a measure of the ocular response of a test subject of claim 1 wherein the visual stimuli are at least one of: geometric shapes, multi-color images, or flashing images.

9. The method of computing a measure of the ocular response of a test subject of claim 1 wherein the step of comparing comprises:

retrieving baseline data indicative of the test subject's abilities to track the visual stimulus from a test subject database; and determining a variance between the measured ability of the test subject's eyes to track the visual stimulus and the retrieved baseline data indicative of baseline values of the test subject's abilities to track the visual stimulus.

10. The method of computing a measure of the ocular response of a test subject of claim 9 wherein the step of comparing further comprises:

converting the determined variance in ability to track the visual stimulus into a scaled score.

11. The method of computing a measure of the ocular response of a test subject of claim 10 wherein the step of comparing further comprises:

measuring at least one physiological characteristic of the test subject selected from the set of physiological characteristics including, but not limited to: pupillography, cognition, balance test results, cognitive test results, blood pressure, and body temperature; and determining a variance between at least one physiological characteristic of the test subject and retrieved baseline data indicative of baseline values of an individual's at least one physiological characteristic of the test subject.

12. The method of computing a measure of the ocular response of a test subject of claim 11 wherein the step of comparing further comprises:

converting the determined variance in ability to track the visual stimulus combined with the determined variance in at least one physiological characteristic of the test subject into a scaled score.

13. The method of computing a measure of the ocular response of a test subject of claim 11 wherein the at least one physiological characteristic of the test subject comprises pupil size, pupil reaction to light stimulation, and hippus.

14. The method of computing a measure of the ocular response of a test subject of claim 11 wherein the at least one physiological characteristic of the test subject comprises blinks or ptosis.

15. A method for computing a measure of the ocular response of a test subject, in response to predetermined stimuli, which are presented on a stimulus presentation display of an ocular measurement device that can be seen by the eyes of the test subject, for viewing by the test subject, comprising:

generating a visual stimulus including visual target movement in at least one of a random pattern, a discontinuous movement, and an oblique direction on the stimulus presentation display, for display to the test subject;

generating, using the ocular measurement device, ocular response test data which measures at least one of the ability of the test subject's eyes to track the visual stimulus and measured pupillary metrics of the test subject's eyes indicative of at least one of a temporal eye movement, a spatial eye movement, pupil size, and pupil reactivity of the test subject in responding to the visual stimulus presently displayed by the stimulus presentation device; and computing a score based on ocular response test data, comprising:

retrieving baseline data from a database, indicative of the test subject's previously measured ocular response test data; and determining a variance between the presently measured test subject's ocular response test data and the retrieved baseline data indicative of the test subject's previously measured ocular response test data.

16. The method of computing a measure of the ocular response of a test subject of claim 15, further comprising:

scanning an iris of the test subject to generate a present set of iris characteristics that are unique to the test subject;

retrieving from a test subject database a previously generated set of iris characteristics that are unique to the test subject;

comparing the presently generated set of iris characteristics that are unique to the test subject with the retrieved previously generated set of iris characteristics that are unique to the test subject; and authenticating, in response to the presently generated set of iris characteristics that are unique to the test subject corresponding to the retrieved previously generated set of iris characteristics that are unique to the test subject, the identity of the test subject.

17. The method of computing a measure of the ocular response of a test subject of claim 16, further comprising:

storing the presently generated set of iris characteristics that are unique to the test subject in the test subject database.

18. The method of computing a measure of the ocular response of a test subject of claim 16 wherein the step of scanning comprises:

mapping the characteristics of the test subject's iris; and plotting distinct iris markings located on the test subject's iris.

19. The method of computing a measure of the ocular response of a test subject of claim 18, further comprising:

storing the presently mapped characteristics of the test subject's iris and the plotted distinct iris markings located on the test subject's iris in the test subject database.

20. The method of computing a measure of the ocular response of a test subject of claim 15 wherein the step of generating ocular response test data comprises:

calculating a speed, which may include rates of change of velocity of the test subject's eye in tracking movement of the visual stimulus.

21. The method of computing a measure of the ocular response of a test subject of claim 15 wherein the step of generating ocular response test data comprises:

calculating the accuracy of the test subject's eye in tracking movement of the visual stimulus.

22. The method of computing a measure of the ocular response of a test subject of claim 15 wherein the step of generating ocular response test data comprises:

calculating the overshoot/undershoot, i.e., Accuracy, of the test subject's eye in tracking movement of the visual stimulus.

23. The method of computing a measure of the ocular response of a test subject of claim 15 wherein the visual stimuli are at least one of geometric shapes, multi-color images, or flashing images.

24. The method of computing a measure of the ocular response of a test subject of claim 15 wherein the step of comparing comprises:

retrieving baseline data indicative of the test subject's abilities to track the visual stimulus from a test subject database; and determining a variance between the measured ability of the test subject's eyes to track the visual stimulus and the retrieved baseline data indicative of baseline values of the test subject's abilities to track the visual stimulus.

25. The method of computing a measure of the ocular response of a test subject of claim 24 wherein the step of comparing further comprises:

converting the determined variance in ability to track the visual stimulus into a scaled score.

26. The method of computing a measure of the ocular response of a test subject of claim 25 wherein the step of comparing further comprises:

measuring at least one physiological characteristic of the test subject selected from the set of physiological characteristics including, but not limited to, pupillography, cognition, balance test results, cognitive test results, blood pressure, and body temperature; and determining a variance between at least one physiological characteristic of the test subject and retrieved baseline data indicative of baseline values of an individual's at least one physiological characteristic of the test subject.

27. The method of computing a measure of the ocular response of a test subject of claim 26 wherein the step of comparing further comprises:
> converting the determined variance in ability to track the visual stimulus combined with the determined variance in at least one physiological characteristic of the test subject into a scaled score.

28. The method of computing a measure of the ocular response of a test subject of claim 26 wherein the at least one physiological characteristic of the test subject comprises pupil size, pupil reaction to light stimulation, and hippus.

29. The method of computing a measure of the ocular response of a test subject of claim 26 wherein the at least one physiological characteristic of the test subject comprises blinks or ptosis.

* * * * *